United States Patent [19]

Levy

[11] Patent Number: 4,661,063

[45] Date of Patent: Apr. 28, 1987

[54] CLAMP FOR USE IN DENTISTRY

[76] Inventor: Guy Levy, 49, Rue Croix de Regnier, 13004 Marseille, France

[21] Appl. No.: 783,708

[22] Filed: Oct. 3, 1985

[30] Foreign Application Priority Data

Oct. 4, 1984 [FR] France .................................. 84 15433

[51] Int. Cl.⁴ .............................................. A61C 5/12
[52] U.S. Cl. .................................................... 433/139
[58] Field of Search ................................. 433/139, 136

[56] References Cited

U.S. PATENT DOCUMENTS 3,857,181 12/1974 Rappaport ........................... 433/139

Primary Examiner—Robert Peshock
Attorney, Agent, or Firm—William A. Drucker

[57] ABSTRACT

A clamp used for supporting a flexible sheet used in dental operations for isolating teeth has two jaws and a spring in the form of a bridge connecting the jaws, the improvement being that the clamp as a whole is made of a plastics material which is capable of resilient deformation and which is permeable to X-rays, for example polycarbonate.

1 Claim, 4 Drawing Figures

CLAMP FOR USE IN DENTISTRY

BACKGROUND OF THE INVENTION

The present invention relates to a clamp for supporting the flexible sheet used for isolating the teeth, during certain dental operations.

The putting into position of an operating field isolating the tooth from the buccal area is a practice which is unanimously advised.

The most current method consists in using a barrier formed by a flexible sheet commonly constituted by a sheet of rubber. This is perforated with a very small diameter (for example of the order of 3 millimeters) and then distended so as to surround the tooth, to be isolated, on which it will be placed.

In order to avoid this sheet of rubber being able to become disengaged off the tooth on which it is installed, in the course of the operation, it is kept in place by a clamp fixed to the neck of the said tooth.

THE PRIOR ART

The clamps used to carry out this function comprise: two hollowed jaws the ends of which are intended to engage into the interdental spaces, and which may be provided, or not, with flanges: and an upper spring connecting the lingual and vestibulary jaws and permitting a firm tightening of the said jaws on the neck of the tooth on which the clamp is placed.

At the present time these clamps are made of non-oxidisable metal. Because of this, they have a certain number of important inconveniences.

They are impermeable to X-rays and, during the carrying out of radiography, they largely mask the anatomy of the tooth and the instruments introduced into the canals, which hinders the practitioners and obliges them to make a large number of photographs orientated at different angles in order to avoid the superimposition of the jaws, the flanges, the spring, and the part of the tooth to be radiographed.

They are burdensome because they necessitate, so as to be re-employable, being made in a non-oxidising metal which can stand up to sterilization at high temperature.

In view of the fact that they are generally made of tempered spring steel, they are not adjustable or are adjustable only with great difficulty to the particular anatomy of the neck of different kinds of teeth, so that the practitioner must possess, for each kind of tooth, a lessor or greater number of clamps ranging from the smallest diameter to the largest.

Their spring, constituted by a curved strip of metal has a flat or substantially flat section and relatively thin opposed edges the contact of which with the edge of the perforation formed in the sheet of rubber constituting the barrier can give rise to a cutting effect capable of causing a commencement of tearing of the said sheet.

OBJECT OF THE INVENTION

The present invention has for its object to provide a new dental clamp permitting the elimination of these inconveniences.

SUMMARY OF THE INVENTION

This clamp is principally distinguished by the fact that it is constructed of a plastics material provided with a capability of resilient deformation and permeable to X-rays.

The dental clamp of plastics material in accordance with the invention gives several important advantages. It permits the production of clear and complete radiographic photographs of the anatomy of the teeth and of the position of the instruments into the channels, which permits a reduction of the number of photographs necessary for the carrying out of certain operations. It also facilitates the production of these photographs. It can be manufactured in an economic manner by a moulding process, thus permitting it to be discarded after use and thereby eliminating the necessity for sterilization at high temperature after use.

Their jaws can easily be adjusted, by milling, to the particular anatomy of the neck of each kind of tooth, which eliminates the necessity for the practitioner to have available numerous clamps of different characteristics for each kind of tooth. Furthermore, the jaws of the clamp can be manufactured with straight edges in such a manner as to permit the practitioner easily to make by himself, by milling, recesses which are perfectly adapted to the particular contour of the neck of the tooth on which the clamp has to be placed.

The spring which connects the jaws can be moulded with a circular or rounded section the contact with which does not have any cutting effect on the edge of the perforation formed in the flexible sheet constituting the barrier.

BRIEF DESCRIPTION OF THE DRAWINGS

The objects, features and advantages mentioned above, as well as others, will appear better from the description which follows and from the accompanying drawings, wherein.

DESCRIPTION OF THE PREFERRED EMBODIMENTS

Figure 2:
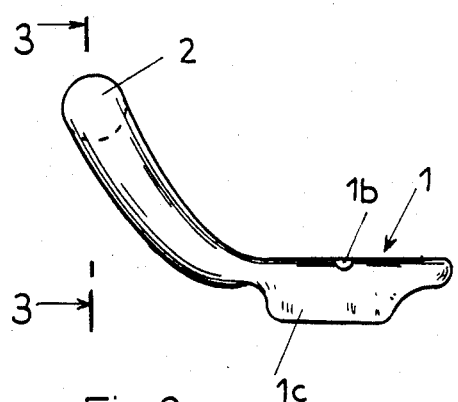
FIG. 2 is a side view of this clamp.

Reference is made to the said drawing for describing advantageous but in no sense limiting examples of construction of the dental clamp of plastics material in accordance with the invention.

This clamp comprises, in known manner, two recessed jaws 1 the ends 1a of which are intended to engage into the interdental spaces, and an upper spring 2 in the form of a bridge connecting the said jaws. The jaws 1 are provided with a perforatiion 1b thanks to which they can be separated by means of a special pair of pliers, opposing the permanent closing force exerted by the spring 2, this pair of pliers permitting convenient placing of the clamp on the tooth and removing it easily also.

The jaws 1 can comprise lateral flanges 1c which are bent and are intended to overlie the gums.

According to the invention the dental clamps are made of a plastics material adapted to bear large resilient deformations and permeable to X-rays. Their manufacture can thus be carried out in various plastics materials having the above-mentioned characteristics, such as polycarbonates for example.

Figure 3:
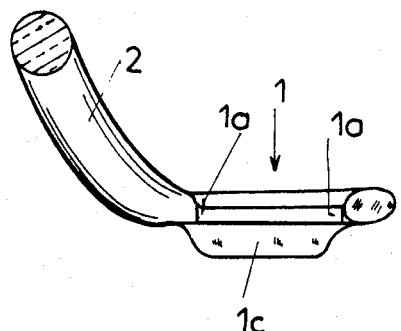
FIG. 3 is a view from the side and in section along the line 3—3 of FIG. 1.
Figure 1:
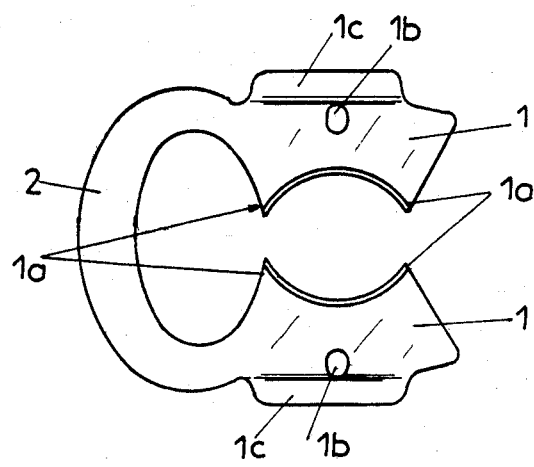
FIG. 1 is a plan view of a dental clamp of plastics material in accordance with the invention.

According to another feature of the invention the spring 2 which connects the two jaws 1 has a circulare or rounded section (FIG. 3).

Figure 4:
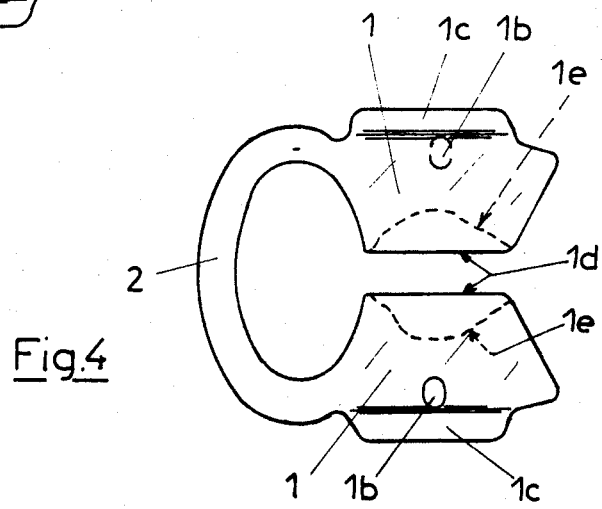
FIG. 4 is a plan view of a variant of construction of this clamp in accordance with which its jaws are provided with a straight edge; the dotted line illustrating recesses which can be made by the practitioner to adjust the said clamp on the neck of a tooth.

By reason of their manufacture of plastics material and more especially, in advantageous manner, of a polycarbonate, the clamps can also be made with the jaws 1 provided with a straight internal edge (FIG. 4). The practitioner thus has the possibility of making himself, with the aid of a small mill which is currently employed in dentistry, the recesses 1e of the jaws 1 so that they will be perfectly adjusted to the particular contour of the neck of the tooth on which the clamp is to be installed.

I claim:

1. In a clamp, for supporting a flexible sheet for isolating a tooth during a dental operation, of the kind having:
   (i) two spaced oppositely-disposed jaws, and
   (ii) resiliently-deformable bridge connecting said jaws and serving as a spring to urge the jaws into contact with a tooth,
the improvement that the jaws and bridge are made as an integral one-piece body of resiliently-deformable polycarbonate material permeable to X-rays, and respective opposed edges of the two jaws, to be presented towards the tooth, are straight and parallel and only narrowly spaced, thereby to present a zone which can be cut back from the edge to provide a recess.

* * * * *